United States Patent [19]

Shimizu et al.

[11] Patent Number: 4,536,496
[45] Date of Patent: Aug. 20, 1985

[54] POLYSACCHARIDES N9GI, THEIR PREPARATION AND THERAPEUTIC COMPOSITIONS CONTAINING THEM

[75] Inventors: Masaki Shimizu, Tokyo; Takeo Nomura, Hino, both of Japan

[73] Assignee: Terumo Kabushiki Kaisha, Tokyo, Japan

[21] Appl. No.: 466,553

[22] Filed: Feb. 15, 1983

[30] Foreign Application Priority Data

Feb. 19, 1982 [JP] Japan .................................. 57-25440
Feb. 19, 1982 [JP] Japan .................................. 57-25441
Dec. 4, 1982 [JP] Japan .................................. 57-212104

[51] Int. Cl.³ .......................... C08B 37/00; C07H 1/00
[52] U.S. Cl. ........................................ 514/54; 536/114; 536/123; 536/127; 536/128
[58] Field of Search ................ 424/180; 536/114, 123, 536/127, 128; 514/54

[56] References Cited

U.S. PATENT DOCUMENTS

| | | | |
|---|---|---|---|
| 2,871,235 | 1/1959 | Jilovice | 536/128 |
| 4,229,440 | 10/1980 | Murofushi et al. | 536/123 |
| 4,304,906 | 12/1981 | Kang et al. | 536/123 |
| 4,366,308 | 12/1982 | Soma et al. | 536/128 |

*Primary Examiner*—Johnnie R. Brown
*Assistant Examiner*—Elli Peselev
*Attorney, Agent, or Firm*—Frishauf, Holtz, Goodman & Woodward

[57] ABSTRACT

A hot-water extract of the bark of *Melia azadirachta* L. is treated with a gel filtrating agent with a fractionation range molecular weight from $1 \times 10^3 - 1 \times 10^5$ to $1 \times 10^3 - 1.5 \times 10^5$. There is obtained polysaccharide N9GI from the first fraction of the three divided polysaccharide fractions. Polysaccharide N9GI further treated with a gel-filtrating agent with a fractionation range molecular weight from $1 \times 10^3 - 2 \times 10^5$ to $1 \times 10^3 - 8 \times 10^5$. There are obtained polysaccharide N9GIa and polysaccharide N9GIb respectively from the first and second fractions of the two divided polysaccharide fractions.

20 Claims, 5 Drawing Figures

POLYSACCHARIDES N9GI, THEIR PREPARATION AND THERAPEUTIC COMPOSITIONS CONTAINING THEM

BACKGROUND OF THE INVENTION

1. Field of the Invention

The present invention relates to novel polysaccharides, their preparation and therapeutic compositions containing them.

More particularly, it is concerned with polysaccharides that are obtained by purifying hot-water extracts of the bark of *Melia azadirachta* L. their preparation and therapeutic compositions containing them. The polysaccharides of the invention are useful for the therapy of a variety of cancers.

2. Description of the Prior Art

It is heretofore known that extracts from *Melia azadirachta* L. show various pharmacological activities. In fact, there are disclosed a method of producing cosmetics for the skin from the bark, leaves, flowers, fruits, root epidermis or resin of *Melia azadirachta* L. by extracting the same with water or a hydrophilic solvent or by finely pulverizing the same (Japanese Patent Publication Nos. 28853/77, 28854/77 and 10125/78); a method of preparing from such raw materials from *Melia azadirachta* L., constituents possessing antimicrobial activities or gastrointestinal or hepatic function-improving activities by extracting the same with hot water (Japanese Patent Publication No. 10124/78); and a method of preparing from such raw materials from *Melia azadirachta* L., constituents effective for the therapy of dermatological and rheumatic diseases by extracting the same with a hydrophobic solvent (Japanese Patent Publication No. 13689/78).

After extensive studies on the pharmacologically active constituents of the bark of *Melia azadirachta* L., we have isolated polysaccharides having anti-tumor activities from hot-water extracts of the bark. It has not been disclosed in the prior arts that the bark of *Melia azadirachta* L. contains polysaccharides.

SUMMARY OF THE INVENTION

It is therefore an object of this invention to provide polysaccharides useful as the anti-cancer agent. Another object is to provide therapeutic compositions containing the polysaccharides. A further object is to provide a process for preparing the polysaccharides.

As described below, the polysaccharides of the invention which are novel substances possess high inhibitory activities against Sarcoma 180 ascites and solid transplanted tumors in mice and Meth A solid transplanted tumor in mice. They are especially effective on fixed solid tumors.

First, according to the present invention, there is provided polysaccharide N9GI obtained from the bark of *Melia azadirachta* L. which has the following physical and chemical characteristics:

(1) Color and appearance

The freeze-dried product is white or pale yellowish brown powder.

(2) Infrared absorption spectrum

Figure 1:
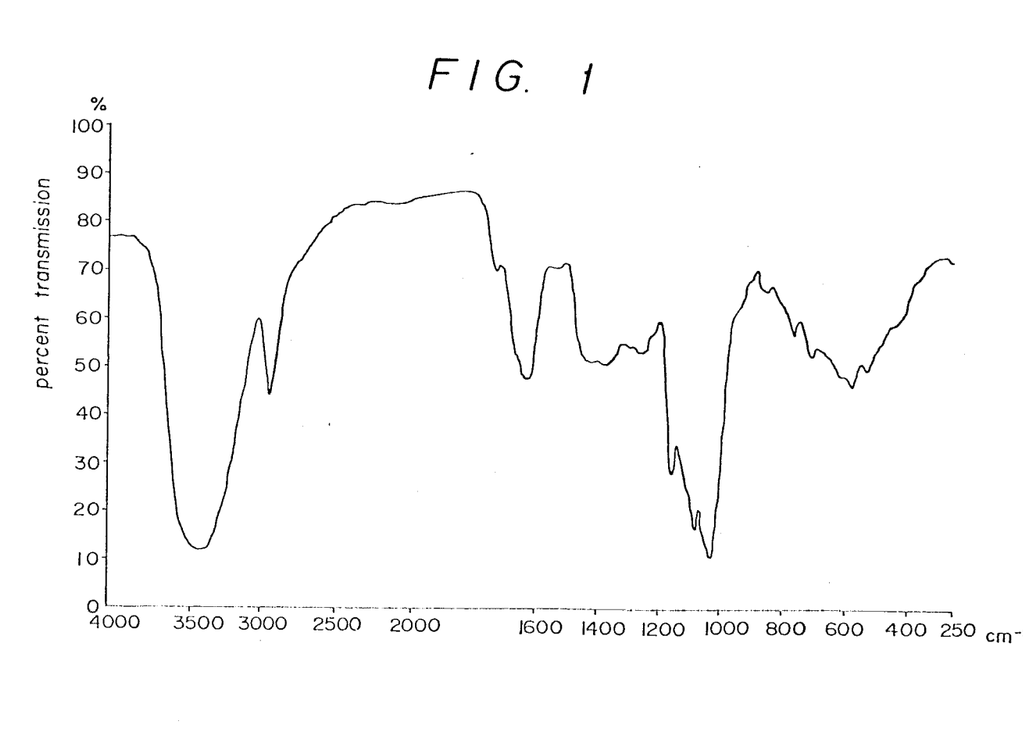
FIG. 1 shows an infrared absorption spectrum of polysaccharide N9GI.

As shown in FIG. 1.

IR$\nu_{max.}^{KBr}$cm.$^{-1}$: 3400, 1630, 1030.

(3) Ultraviolet absorption spectrum

When measured in aqueous solution, there is no absorption maximum with end absorption only observed.

(4) Solubility

Soluble in water but insoluble in organic solvents such as methanol, ethanol, acetone, ether, chloroform, ethyl acetate, benzene, hexane and the like.

(5) Color reaction

Phenol sulfate reaction and anthrone sulfate reaction are positive. It turns to greenish blue by the addition of iodine.

Secondly, according to the invention, there is provided a process for preparing polysaccharide N9GI having the physical and chemical characteristics as described above which comprises extracting the bark of *Melia azadirachta* L. with hot water, purifying said extract by means of precipitation with an alcohol or of a permeable membrane, dissolving the purified product thus obtained in water, treating said aqueous solution with a molecular sieving agent with a fractionation range molecular weight from about $1 \times 10^{3} - 1 \times 10^{5}$ to $1 \times 10^{3} - 1.5 \times 10^{5}$ and isolating the first fraction of the three divided polysaccharide fractions.

Thirdly, according to the invention, there is provided polysaccharide N9GIa obtained from the bark of *Melia azadirachta* L. which has the following structure and characteristics:

(1) Structure

A neutral polysaccharide which contains as the main chain α-(1→4)-glucan connected with arabinose by an α-(1→6) bond and is composed of glucose and arabinose at a ratio of ca. 5:1.

(2) Color and appearance

The freeze-dried product is a white powder.

(3) Solubility

Soluble in water but insoluble in organic solvents such as methanol, ethanol, acetone, ether, chloroform, ethyl acetate, benzene, hexane and the like.

(4) Color reaction

Phenol sulfate reaction and anthrone sulfate reaction are positive. It turns to greenish blue by the addition of iodine.

(5) Molecular weight

A column gel chromatography using dextran gel with a fractionation range molecular weight of $1 \times 10^{3} - 2 \times 10^{5}$ gives a single peak with a molecular weight being ca. 94,000.

(6) Specific rotation $[\alpha]_D^{22}$: $-35°$ (c=0.4, H$_2$O).

(7) Infrared absorption spectrum

Figure 2:
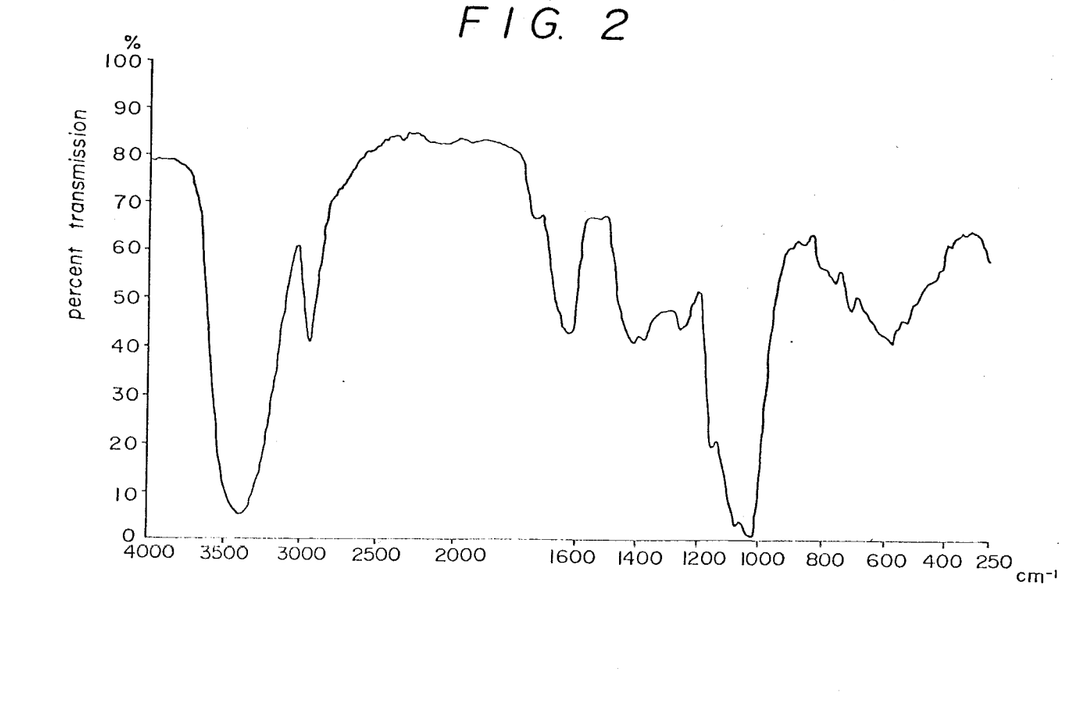
FIGS. 2 and 3 respectively show an infrared absorption spectrum and a $^{13}$C nuclear magnetic resonance spectrum of polysaccharide N9GIa.
Figure 3:
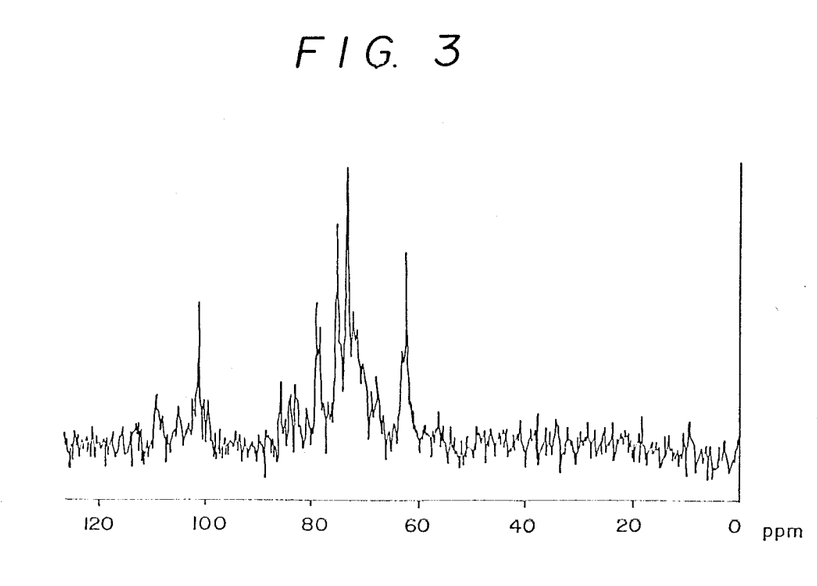

As shown in FIG. 2.

IR$\nu_{max.}^{KBr}$ cm.$^{-1}$: 3400, 2930, 1620.

(8) Ultraviolet absorption spectrum

Measured in aqueous solution, there is no absorption maximum with end absorption only observed.

(9) $^{13}$C nuclear magnetic resonance spectrum

Figure 4:
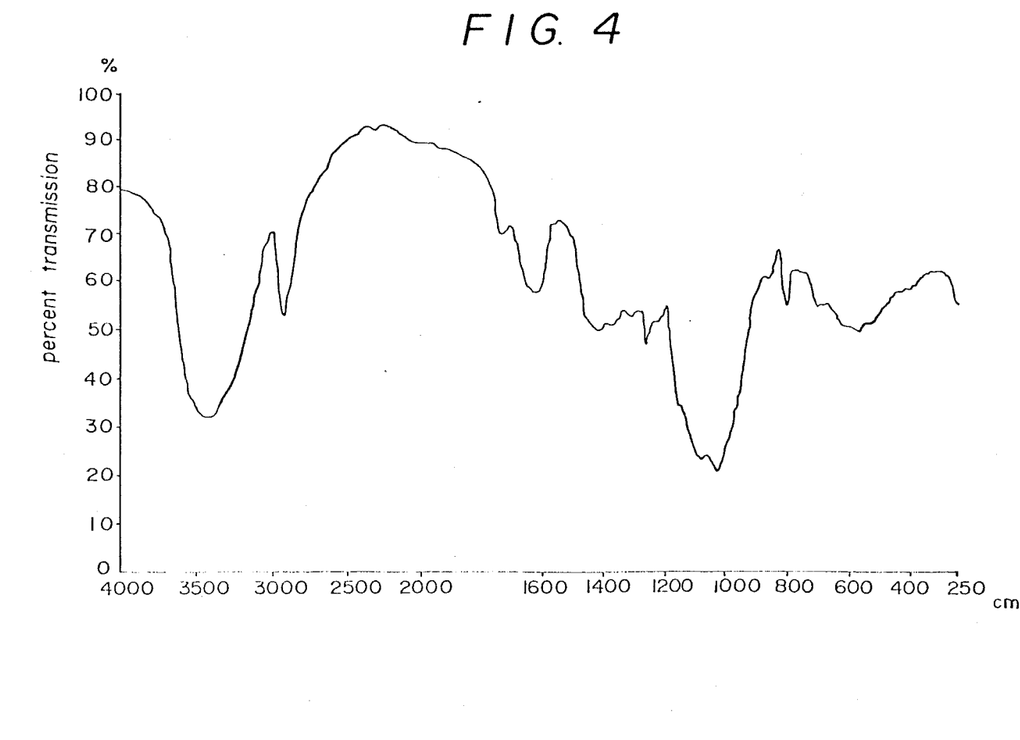
FIGS. 4 and 5 respectively show an infrared absorption spectrum and a $^{13}$C nuclear magnetic resonance spectrum of polysaccharide N9GIb.

A 100 MHz $^{13}$C nuclear magnetic resonance spectrum measured in deuterium oxide using as the external standard TMS (tetramethylsilane) is shown in FIG. 4.

Fourthly, according to the invention, there is provided a process for preparing polysaccharide N9GIa having the structure and characteristics as described above which comprises treating the hot-water extract of the bark of *Melia azadirachta* L. with a molecular sieve to isolate a compound having a molecular weight of ca. 94,000.

Fifthly, according to the invention, there is provided polysaccharide N9GIb obtained from the bark of *Melia azadirachta* L. which has the following structure and characteristics:

(1) Structure

A neutral polysaccharide which contains as the main chain α-(1→4)-glucan interspersed with β-(1→3)-fucose and branched with α-(1→6)-arabinose and is composed of glucose, arabinose and fucose at a ratio of ca. 5:2:1.

(2) Color and appearance

The freeze-dried product is a white powder.

(3) Solubility

Soluble in water but in soluble in organic solvents such as methanol, ethanol, acetone, ether, chloroform, ethyl acetate, benzene, hexane and the like.

(4) Color reaction

Phenol sulfate reaction and anthrone sulfate reaction are positive. It turns to greenish blue by the addition of iodine.

(5) Molecular weight

A column gel chromatography using dextran gel with a fractionation range molecular weight of $1 \times 10^3 - 2 \times 10^5$ gives a single peak with a molecular weight being ca. 21,000.

(6) Specific rotation $[\alpha]_D^{22}$: −46° C. (c=0.28, H$_2$O).

(7) Infrared absorption spectrum

As shown in FIG. 4.

IR$\nu_{max}^{KBr}$ cm.$^{-1}$: 3400, 2930, 1630.

(8) Ultraviolet absorption spectrum

Figure 5:
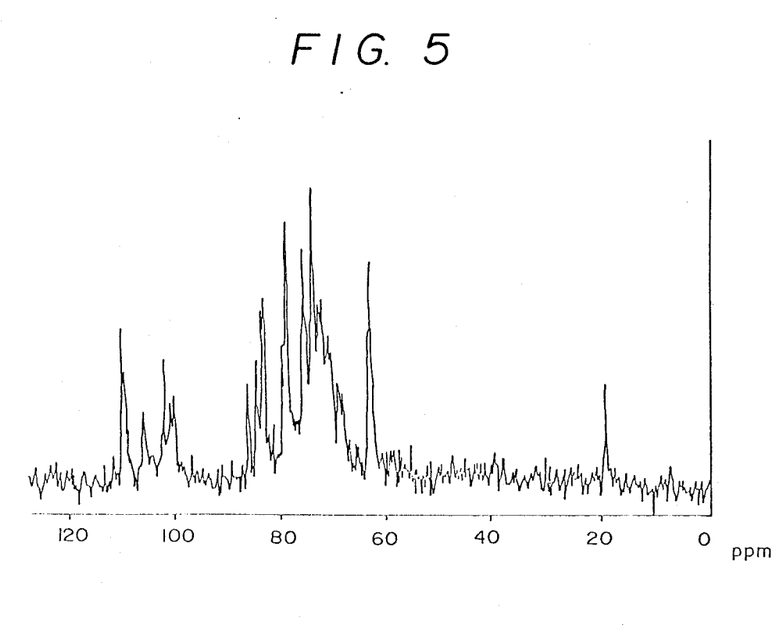

Measured in aqueous solution, there is no absorption maximum with end absorption only observed. (9) $^{13}$C nuclear magnetic resonance spectrum A 100 MHz $^{13}$C nuclear magnetic resonance spectrum measured in deuterium oxide using as the external standard TMS (tetramethylsilane) is shown in FIG. 5.

Sixthly, according to the present invention, there is provided a process for preparing polysaccharide N9GIb having the structure and characteristics as described above which comprises subjecting a hot-water extract of the bark of *Melia azadirachta* L. to treatment with a molecular sieve thereby isolating a compound having a molecular weight of ca. 21,000.

DETAILED DESCRIPTION OF THE INVENTION

The plant used in the present invention as the starting material is scientifically called *Melia azadirachta* L. or *Azadirachta indica* Juss, which is a large tree 10 m. or higher in height and native in the tropics. In the process according to the present invention, hot-water extracts of the bark of this plant is employed as the polysaccharide source. The bark harvested in any season of the year may be used as the starting material. The hot-water extraction of the bark of *Melia azadirachta* L. is operated by conventional procedures. As a matter of fact, it is carried out by adding to a finely divided bark hot water at approximately 80° C. or higher or by adding water to the bark and heating the mixture to boiling. The heating may be conducted in a boiling-water bath or over a direct heat. While the heating period of time is dependent upon the quality of the starting material and other factors, it is usually from 1 to 48 hours. After completion of the extraction, the extraction mixture is subjected to filtration to give an extract. As the hot-water extract of the bark of *Melia azadirachta* L. thus obtained contains a large amount of impurities, it is desirable to purify said extract, prior to the molecular sieving step of the invention, by means of an alcohol precipitation or of a permeable membrane. For example, when the purification is conducted by means of an alcohol precipitation, an alcohol such as methanol or ethanol is added to the aforementioned extract, and precipitates thus formed are isolated, for example, by means of centrifugal separation to obtained the desired extract. When a permeable membrane is used for the purification, said extract is placed in a permeable membrane, which is then immersed in water to effect dialysis. If desired, the dialyzate is concentrated to dryness or freeze-dried to yield the desired extract. As the permeable membrane is used regenerated cellulose with a fractionation range molecular weight of 50,000 or less, for example, Spectra Por 1-6 (manufactured by Spectrum Medical Industries Co.) or Visking Tube (manufactured by Union Carbide Co.). The starting material in the process of the present invention, hot-water extract of the bark of *Melia azadirachta* L. is prepared by dissolving the extract after purification by means of a permeable membrane or of an alcohol precipitation in water. Besides, it is also desirable to remove useless constituents, prior to the hot-water extraction of the bark of *Melia azadirachta* L., by subjecting the bark to pretreatment with an organic solvent and/or water at room temperature. As the solvent used for the pretreatment are mentioned polar organic solvents such as methanol, ethanol, propanol, pyridine and acetone and non-polar organic solvents such as benzene, toluene, xylenes, n-hexane, chloroform, carbon tetrachloride and ethyl acetate.

The treatment with a molecular sieve for the separation of the polysaccharides according to the present invention is carried out preferably by gel filtration by means of a gel filtrating agent. As the gel filtrating agent dextran gel, polyacrylamide gel, polyvinyl polymer gel, porous glass beads and the like are preferred.

The polysaccharide N9GI of the invention is prepared by passing the aforementioned hot-water extract of the bark of *Melia azadirachta* L. through a column packed with a gel filtrating agent with a fractionation range molecular weight from about $1 \times 10^3 - 1 \times 10^5$ to $1 \times 10^3 - 1.5 \times 10^5$, eluting the column with distilled water, collecting the first fraction of the three divided polysaccharide fractions and evaporating to dryness or freeze-drying the collected fraction. The elution is carried out while detecting elution of the polysaccharide by such a method as the phenol sulfate method in accordance with the conventional procedures. As the gel filtrating agent with a fractionation range molecular weight from about $1 \times 10^3 - 1 \times 10^5$ to $1 \times 10^3 - 1.5 \times 10^5$, Sephadex G-100 [manufactured by Pharmacia Co., Sweden] which is a dextran gel, Biogel P-100 (manufactured by Biorad Co., U.S.A.) which is a polyacrylamide gel, Toyopal HW-55 (manufactured by Toyo Soda Industries) which is a polyvinyl polymer gel, and CPG-10 (manufactured by Electro-Nucleonics, U.S.A.) which is porous beads are preferred.

Polysaccharides N9GIa and N9GIb are respectively obtained by subjecting the hot-water extract of the bark of *Melia azadirachta* L. to a molecular sieving treatment to isolate a polysaccharide having a molecular weight of ca. 94,000 and a polysaccharide having a molecular weight of ca. 21,000.

Preferably, a fraction containing the aforementioned polysaccharide N9GI or an aqueous solution of polysaccharide N9GI is further passed through a column packed with a gel filtrating agent with a fractionation range molecular weight from about $1 \times 10^3$–$2 \times 10^5$ to $1 \times 10^3$–$8 \times 10^5$, the column is eluted with distilled water and polysaccharide N9GIa is obtained from the first fraction of the two divided polysaccharide fractions and polysaccharide N9GIb from the second polysaccharide fraction.

As the gel-filtering agent with a fractionation range molecular weight from about $1 \times 10^3$–$2 \times 10^5$ to $1 \times 10^3$–$8 \times 10^5$, Sephadex G-200, Sephacril S-300 (manufactured by Pharmacia Co., Sweden) which are dextran gels, Biogel P-300 (manufactured by Biorad Co., U.S.A.) which is a polyacrylamide, Toyopal HW-60 (manufactured by Toyo Soda Industries) which is a polyvinyl polymer, porous beads CPG-10 and the like are preferred.

Polysaccharide N9GI of the present invention is considered to be a mixture of polysaccharide N9GIa and polysaccharide N9GIb. Pharmacological studies have revealed that it possesses marked inhibitory activities against Sarcoma 180 ascites and solid transplanted tumors in mice and Meth A solid transplanted tumor in mice. It has also been demonstrated that polysaccharides N9GIa and N9GIb exert similar pharmacological activities. Therefore, separation of polysaccharide N9GI into polysaccharide N9GIa and polysaccharide N9GIb is not necessary for use as the anti-cancer agent. It is practical to use a mixture of the two, that is, as polysaccharide N9GI.

The following reference example, examples and pharmacological tests further illustrate the invention:

REFERENCE EXAMPLE

Preparation of a hot-water extract of the bark of *Melia azadirachta* L.

(1) Pretreatment was carried out of 50 g. of dried bark of *Melia azadirachta* L. by extracting the same with benzene ($3 \times 500$ ml.) and methanol ($3 \times 500$ ml.) at room temperature for 24 hours. The residue thus obtained from the extraction was extracted with three 200-ml. portions of hot water. The combined extracts were concentrated on a rotary evaporator to dryness to give 1960.5 mg. of powders.

(2) To a solution of 1000 mg. of the powders produced under (1) above in 200 ml. of water was slowly added pure ethanol with stirring at room temperature to an ethanol concentration of 80% in the aqueous solution. There were then formed precipitates, which were isolated by centrifugal separation to obtain 594.5 mg. of brown powders.

(3) A solution of 500 mg. of the powders obtained under (1) above in 50 ml. of water was placed in Specta Por 6 (fractionation range molecular weight 50,000) for dialysis against water. The dialyzate was concentrated on a rotary evaporator to dryness to give 310 mg. of brown powders.

EXAMPLE 1

Preparation of polysaccharide N9GI

A solution of 1020 mg. of the hot-water extract of the bark of *Melia azadirachta* L. obtained in the above reference example under (2) or (3) in 20 ml. of distilled water was poured onto a column (7.0 cm. in diameter and 35.0 cm. in length) packed with Sephadex G-100, and the gel filtration was carried out using distilled water. Sugar content in the eluate was assayed by the phenol sulfate method during the gel filtration. There were obtained polysaccharide in three fractions. When the solvent was distilled off from the first eluate fraction, there were produced 273 mg. of desired polysaccharide N9GI.

A similar result was produced by using Biogel P-100 in place of the gel-filtrating agent Sephadex G-100 in the above process.

EXAMPLE 2

Preparation of polysaccharides N9GIa and N9GIb

A solution of 50 mg. of polysaccharide N9GI produced in Example 1 in 5 ml. of distilled water was poured onto a column (4.0 cm. in diameter and 50.0 cm. in length) packed with Sephadex G-200, and the gel filtration was carried out using distilled water. Sugar content in the eluate was assayed by the phenol sulfate method during the gel filtration. There were obtained polysaccharides in two fractions. The first polysaccharide fraction yielded 18 mg. of polysaccharide N9GIa, and the second one yielded 16 mg. of polysaccharide N9GIb. These polysaccharides were found to be respectively a single compound by means of high performance liquid chromatography and electrophoresis.

A similar result was produced by using Sephacril S-300 in place of the Sephadex G-200 in the above gel filtration.

The structures and characteristics of polysaccharides N9GI, N9GIa and N9GIb are as mentioned above, where IR absorption spectrum was measured by KBr method using "Hitachi Infrared Spectrophotometer Model 295" (product of Hitachi Ltd.), UV absorption spectrum was measured by using methanol as a solvent by using "Hitachi Doublebeam spectrophotometer Model 200-20" (product of Hitachi Ltd.) and $^{13}C$ nuclear magnetic resonance spectrum was measured by using "JEOL FX-100" (product of Japan Electron Optics Laboratory Co., Ltd.).

Results of the pharmacological tests on polysaccharides N9GI, N9GIa and N9GIb of the present invention will be described below.

TEST EXAMPLE 1

Effect on Sarcoma 180 ascites tumor (Preparation of the test material)

In a suspension of 0.5% carboxymethylcellulose (CMC) in phosphate buffer saline solution (manufactured by Gibco, containing 9.5 mM phosphate; PBS) was dissolved the test material to a predetermined concentration.

(Transplantation of Sarcoma 180 tumor cells)

Sarcoma 180 tumor cells subcultivated in the abdominal cavity of a mouse were withdrawn and diluted with physiological saline solution to a cell count of $1.0 \times 10^8$/ml. The cell suspension was transplanted intraperitoneally in male ICR mice 4 weeks old by means of a syringe in an amount of 0.5 ml. per mouse. Number of the transplanted cells per mouse is calculated to be $1.0 \times 10^7$.

(Administration of test material)

On the next day of the Sarcoma 180 tumor cell transplantation, the test material prepared as above was intraperitoneally administered by means of a syringe at a dose of 0.1 ml./mouse, and the administration was made once a day for 4 days in total. Six mice were employed for each concentration of each test material. As the control was employed the CMC-containing PBS, the solvent for the test material, which was administered in the same way. The dose was expressed in terms of mg. per kg. bodyweight of the mouse.

(Method of evaluation)

On the 7th day of the tumor cell transplantation, body-weight of each mouse was measured. Then, the ascites accumulated in the abdominal cavity was thoroughly withdrawn, and bodyweight of the mouse was measured. Difference in bodyweight before and after withdrawal of the ascites is taken as the amount of ascites.

The withdrawn ascites was then introduced into a hematocrit tube and then centrifuged on a hematocrit rotar at a low temperature to give an ascites value (proportion of the tumor cells in the ascites) which corresponded to the blood hematocrit value. This value multiplied by the volume of ascites gives the volume of cells present in the whole ascites. This is designated as the total packed cell volume (TPCV). In the case of control, the total volume of ascites was 6-10 ml., and the TPCV was 1.6-2.5 ml.

Effect on the tumor was rated poor (−) when the TPCV ratio of the test material-administered mice to the control mice (T/C) was 100-66%, fair (+) when it was 65-41%, good (++) when it was 40-11% and excellent (+++) when it was 1-0%. Results are shown in Table 1.

TEST EXAMPLE 2

TABLE 1

Effects on Sarcoma 180 transplanted tumors (mice)

| Test material | Dose mg./kg. | Ascites tumor T/C (%) | Evaluation | Solid tumor T/C (%) | Evaluation |
|---|---|---|---|---|---|
| Polysaccharide N9GI | 75 | 60 | + | 43 | ++ |
|  | 50 | 46 | ++ | 26 | ++ |
|  | 25 | 52 | + | 34 | ++ |
|  | 5 | 100 | − | 100 | − |
| Polysaccharide N9GIa | 75 | 21 | ++ | 43 | ++ |
|  | 50 | 23 | ++ | 61 | + |
|  | 25 | 25 | ++ | 70 | + |
|  | 5 | 17 | ++ | 98 | − |
| Polysaccharide N9GIb | 75 | 22 | ++ | 64 | + |
|  | 50 | 24 | ++ | 77 | − |
|  | 25 | 30 | ++ | 103 | − |
|  | 5 | 43 | + | 105 | − |

TEST EXAMPLE 3

Effect on Sarcoma 180 solid tumor

Preparation of the test material, transplantation of Sarcoma 180 tumor cells, administration of the test material and evaluation of the effect were made in the same way as in Test Example 2 except that administration of the test material was made in three ways: Administrations on the day 1st, 3rd, 5th, 7th and 9th of tumor cell transplantation once a day, consecutive administrations from the 1st day of transplantation once a day for 10 days and consective administrations from the 1st day of transplantation once a day for 20 days. The effect was evaluated on the 35th day of tumor cell transplantation by resecting the tumor tissue. Results are shown in Table 2.

TABLE 2

Effect on Sarcoma 180 solid tumor (mice)

| Test material | Dose (mg./kg.) | Day of administration 1,3,5,7 & 9th T/C (%) | Evaluation | 1st–10th T/C (%) | Evaluation | 1st–20th T/C (%) | evaluation |
|---|---|---|---|---|---|---|---|
| Polysaccharide N9GI | 50 | 4 | (+++) 7/9* | 7 | (+++) 5/7 |  |  |
|  | 25 | 11 | (+++) 5/9 |  |  |  |  |
|  | 10 | 68 | (+) 1/9 | 24 | (++) 5/10 | 6 | (+++) 7/11 |
|  | 2 | 74 | (−) |  |  | 53 | (+) 2/11 |

*indicates the proportion of mice in which the tumor tissue was completely involuted.

Effect on Sarcoma 180 solid tumor (Transplantation of Sarcoma 180 tumor cells)

Cell suspension at a concentration of $1.0 \times 10^8$ cells/ml. was prepared in the same way as in Test Example 1. The cells were transplanted subcutaneously on the back of male ICR mice 4 weeks old at a dose of 0.1 ml. per mouse by means of a syringe.

(Administration of the test material)

On the 21st day of the tumor cell transplantation, grown tumor tissue was resected and weighed (average for a group of 6 animals). The effect was evaluated on the basis of ratio of the average weight for the treated animals to that of the control animals (T/C). The weight of tumor tissue for the control animals was 3.0-4.5 g. The effect was rated poor (−) when the ratio was 100-71%, fair (+) when it was 70-51%, good (++) when it was 50-21% and excellent (+++) when it was 20-0%. Results are shown in Table 1.

TEST EXAMPLE 4

Effect on fixed solid tumor

Sarcoma 180 cells were transplanted subcutaneously on the back of male ICR mice (10 animals) at a dose of $1 \times 10^7$ cells per animals, and the mice were bred. From the 10th day when the solid tumor was completely fixed and grown to a size of about 1-2 g., administration of a predetermined dose of the test material was made intraperitoneally once a day for 5 days. The tumor on the 21st day of the transplantation was cut, and the weight was compared with that for the control group. The effect was evaluated according to the method in Test Example 2. Results are shown in Table 3.

TABLE 3

| Test material | Effect on fixed solid tumor Dose (mg./kg.) | T/C (%) | Evaluation |
|---|---|---|---|
| Polysaccharide N9GI | 100 | 6 | +++ |
|  | 50 | 15 | +++ |
|  | 25 | 33 | ++ |

TABLE 3-continued

| Test material | Effect on fixed solid tumor | | |
|---|---|---|---|
| | Dose (mg./kg.) | T/C (%) | Evaluation |
| | 10 | 39 | ++ |
| Polysaccharide N9GIa | 100 | 5 | +++ |
| | 50 | 7 | +++ |
| | 25 | 22 | ++ |
| | 10 | 47 | ++ |
| Polysaccharide N9GIb | 100 | 18 | +++ |
| | 50 | 25 | ++ |
| | 25 | 39 | ++ |
| | 10 | 54 | + |

TEST EXAMPLE 5

Effect on fixed solid tumor

Effects on fixed solid tumor were tested in the same way as in Test Example 4 except that administrations of the test material were made in three ways: Consecutive administrations from the 6th day to the 10th day of the tumor cell transplantation once a day, from the 6th day to the 15th day once a day and from the 11th day to the 20th day once a day. The effect was evaluated on the 35th day of the tumor cell transplantation. Results are shown in Table 4.

TABLE 4

| | | Effects on fixed solid tumor (mice) | | | | | |
|---|---|---|---|---|---|---|---|
| | | Day of administration | | | | | |
| Test material | Dose (mg./kg.) | 6th–10th | | 6th–15th | | 11th–20th | |
| | | T/C (%) | Evaluation | T/C (%) | Evaluation | T/C (%) | Evaluation |
| Polysaccharide N9GI | 50 | 6 | (+++) 7/9* | 3 | (+++) 4/6 | 5 | (+++) 5/7 |
| | 25 | 3 | (+++) 7/10 | — | — | — | — |
| | 10 | 57 | (+) 1/10 | 1 | (+++) 8/9 | 7 | (+++) 8/10 |

*indicates the proportion of mice in which the tumor tissue was completely involuted.

As evidently seen from Tables 1–4 above, polysaccharides N9GI, N9GIa and N9GIb of the present invention possess high inhibitory activities against Sarcoma 180 ascites and solid tumors and fixed solid tumor by intraperitoneal administration.

TEST EXAMPLE 6

Effect on Sarcoma 180 solid tumor by oral administration

Effects of the polysaccharides of the invention by oral administration on Sarcoma 180 solid tumor were tested under the same conditions as in Test Examples 2 and 3 except that the dose of the transplanted cells was $2 \times 10^6$ cells per mouse and evaluation was made on the basis of the weight on the 32nd day. The test material in a predetermined concentration was administered forcibly into the stomach by means of a stomach probe at a dose of 0.1 ml./administration/mouse. Results are shown in Table 5.

TABLE 5

| | | Effects on Sarcoma 180 solid tumor by oral administration (mice) | | | | | |
|---|---|---|---|---|---|---|---|
| | | Day of administration | | | | | |
| Test material | Dose (mg./kg.) | 1,3,5,7,9th | | 7,9,11,13,15th | | 5,7,9 ... 19,21,23rd | |
| | | T/C (%) | Evaluation | T/C (%) | Evaluation | T/C (%) | Evaluation |
| Polysaccharide N9GI | 250 | 44 | (++) | 54 | (+) | 57 | (+) |
| | 50 | 80 | (−) | 71 | (−) | 95 | (−) |

From Table 5, it is clear that the polysaccharide of the invention possesses an anti-tumor activity at a dose of 250 mg./kg. bodyweight also by oral administration.

TEST EXAMPLE 7

Effect on Meth A fibroblastosarcoma

The cells of Meth A fibroblastosarcoma subcultivated in the abdominal cavity of a Balb/C mouse were withdrawn together with the ascites and diluted with physiological saline solution to adjust the cell count to $1.0 \times 10^7$ cells per ml. The cell suspension was transplanted subcutaneously on the back of male Balb/C mice 5 weeks old at a dose of 0.1 ml. per animal by means of a syringe. The number of the transplanted cells per animal is $1.0 \times 10^6$. The test material was prepared in the same way as in Test Examples 2 and 3 and was intraperitoneally administered on a predetermined day. Evaluation was made by resecting the sarcoma tissue on the 21st day of the sarcoma cell transplantation and measuring its weight. Results are shown in Table 6.

TABLE 6

| | | Effect on Meth A fibroblastosarcoma (mice) | | | | | |
|---|---|---|---|---|---|---|---|
| | | Day of administration | | | | | |
| Test material | Dose (mg./kg.) | 5,7,9,11,13 ... 19th | | 6–15th | | 11–20th | |
| | | Weight of sarcoma (g.) | Ratio of inhibition (%) | Weight of sarcoma (g.) | Ratio of inhibition (%) | Weight of sarcoma (g.) | Ratio of inhibition (%) |
| Polysaccharide N9GI | 100 | 4.04 | 39 ($P < 0.01$)* | 3.31 | 47 | 4.56 | 28 ($P < 0.05$) |
| | 25 | 4.74 | 29 ($P < 0.02$) | 5.49 | 12 | 5.08 | 19 ($P < 0.02$) |
| | 5 | 5.16 | 22 | 6.08 | 3 | 5.07 | 20 ($P < 0.05$) |

TABLE 6-continued

| | | Effect on Meth A fibroblastosarcoma (mice) | | | | | |
|---|---|---|---|---|---|---|---|
| | | Day of administration | | | | | |
| | | 5,7,9,11,13 ... 19th | | 6-15th | | 11-20th | |
| Test material | Dose (mg./kg.) | Weight of sarcoma (g.) | Ratio of inhibition (%) | Weight of sarcoma (g.) | Ratio of inhibition (%) | Weight of sarcoma (g.) | Ratio of inhibition (%) |
| Control group | | 6.64 | — | 6.27 | — | 6.31 | — |

*significance level by the t-test.

As shown in Table 6, the polysaccharide of the present invention possesses a significant growth-inhibitory activity also against Meth A fibroblastosarcoma, an isogenic tumor when administered 8–10 times at a dose of 100 mg./kg.

TEST EXAMPLE 8

Acute toxicity

Acute toxicity tests were conducted respectively for polysaccharides N9GI, N9GIa and N9GIb using male ICR mice weighing 20±1 g. $LD_{50}$ values were higher than 600 mg./kg. by intraperitoneal administration and higher than 1000 mg./kg. by oral administration with any of the polysaccharides.

As evidently demonstrated by the pharmacological tests above, the polysaccharides of the present invention possess marked anti-tumor activities and are very low in toxicity. It is also expected from their especially high inhibitory activities against fixed solid tumors that the polysaccharides of the invention possess anti-tumor activities of the immunoactivation type.

The polysaccharides of the invention are formulated optionally with pharmaceutical carriers or excipients.

Formulations for oral administrations such as tablets, powders, capsules and granules may contain conventional excipients, for example, calcium carbonate, calcium phosphate, corn starch, potato starch, sucrose, lactose, talc, magnesium stearate, gum arabic and the like. The liquid preparation for oral administration may be aqueous or oily suspension, solution, syrup, elexir and the like.

The injectable preparation is in the form of a solution or suspension and may contain excipients such as suspending agent, stabilizer or dispersing agent. It may also contain sterile distilled water, purified oil such as peanut oil or corn oil, or non-aqueous solvent such as polyethylene glycol or polypropylene glycol.

A preferred formulation is a pharmaceutical preparation in dosage unit form comprising per unit dosage from 10–500 mg. of the polysaccharides of the invention and a pharmaceutical diluent.

We claim:

1. Polysaccharide N9GI obtained from the bark of *Melia azadirachta L.* which has the following characteristics:

the freeze dried product of said polysaccharide N9GI is a white or pale yellowish brown powder;

said polysaccharide N9GI;

has an infrared absorption spectrum as shown in FIG. 1, wherein $IR\nu_{max.}^{KBr}cm.^{-1}$: 3400, 1630, 1030;

has an ultraviolet absorption spectrum which shows no absorption maximum with end absorption only when measured in an aqueous solution;

is soluble in water and insoluble in organic solvents selected from methanol, ethanol, acetone, ether, chloroform, ethyl acetate, benzene, and hexane;

reacts with phenol sulfate and anthrone sulfate; and turns greenish blue by reaction with iodine;

said polysaccharide N9GI is a mixture of polysaccharide N9GIa and of polysaccharide N9GIb;

said polysaccharide N9GIa;

is a neutral polysaccharide which contains as the main chain thereof an $\alpha$-(1→4)-glucan connected to arabinose by an $\alpha$-(1→6) bond and is composed of glucose and arabinose at a ratio of about 5:1;

is soluble in water and insoluble in organic solvents selected from methanol, ethanol, acetone, ether, chloroform, ethyl acetate, benzene and hexane;

reacts with phenol sulfate and anthrone sulfate;

turns to greenish blue by reaction with iodine;

when analyzed by column gel chromatography using dextran gel with a fractionation range molecular weight of $1 \times 10^3 - 2 \times 10^5$ gives a single peak with a molecular weight of about 94,000;

has a specific rotation of $(\alpha)_D^{22}$: $-35°$ (c=0.4, $H_2O$);

has an infrared absorption spectrum as shown in FIG. 2, wherein $IR\nu_{max.}^{KBr}cm.^{-1}$: 3400, 2930, 1620;

has an ultraviolet absorption spectrum which shows no absorption maximum with end absorption only when measured in an aqueous solution; and has a 100 MHz $^{13}C$ nuclear magnetic resonance spectrum measured in deuterium oxide using TMS (tetramethylsilane) as the external standard as shown in FIG. 4; and said polysaccharide N9GIb;

is a neutral polysaccharide which contains as the main chain thereof an $\alpha$-(1→4)-glucan interspersed with $\beta$-(1→3)-fucose and branched with $\alpha$-(1→6)-arabinose and is composed of glucose, arabinose and fucose at a ratio of about 5:2:1;

is soluble in water and insoluble in organic solvents selected from methanol, ethanol, acetone, ether, chloroform, ethyl acetate, benzene, and hexane;

reacts with phenol sulfate and anthrone sulfate;

turns greenish blue by reaction with iodine;

when analyzed by column gel chromatography using dextran gel with a fractionation range molecular weight of $1 \times 10^3 - 2 \times 10^5$ gives a single peak with a molecular weight of about 21,000;

has a specific rotation of $(\alpha)_D^{22}$: $-46°$ C. (c=0.28, $H_2O$);

has an infrared absorption spectrum as shown in FIG. 4, wherein $IR\nu_{max.}^{KBr}cm.^{-1}$: 3400, 2930, 1630;

has an ultraviolet absorption spectrum which shows no absorption maximum with end absorption only when measured in an aqueous solution;

has a 100 MHz $^{13}C$ nuclear magnetic resonance spectrum measured in deuterium oxide using TMS (tetramethylsilane) as the external standard as shown in FIG. 5.

2. A therapeutic composition characterized by inhibiting the growth of Sarcoma 180 transplanted tumor tissue in mice comprising an effective amount of the polysaccharide according to claim 1 and a pharmaceutical diluent.

3. The therapeutic composition of claim 2 in unit dosage form wherein the effective amount per unit dosage is 10 to 500 mg.

4. A process for preparing polysaccharide N9GI which comprises extracting the bark of *Melia azadirachta L.* with hot water, treating the hot water extract by means of precipitation with an alcohol or with a permeable membrane to thereby form a purified extract, dissolving the purified extract in water to form an aqueous solution of said purified extract, treating said aqueous solution with a molecular sieving agent having a fractionation range molecular weight from $1 \times 10^3 - 1 \times 10^5$ to $1 \times 10^3 - 1.5 \times 10^5$ to thereby obtain three divided polysaccharide fractions and isolating the first fraction of the three divided polysaccharide fractions; said polysaccharide N9GI having the following characteristics:

the freeze dried product of said polysaccharide N9GI is a white or pale yellowish brown powder;
said polysaccharide N9GI;
has an infrared absorption spectrum as shown in FIG. 1, wherein $IR\nu_{max}.^{KBr}cm.^{-1}$: 3400, 1630, 1030;
has an ultraviolet absorption spectrum which shows no absorption maximum with end absorption only when measured in an aqueous solution;
is soluble in water and insoluble in organic solvents selected from methanol, ethanol, acetone, ether, chloroform, ethyl acetate, benzene, and hexane;
reacts with phenol sulfate and anthrone sulfate; and
turns greenish blue by reaction with iodine.

5. The process of claim 4, wherein the step of treating said aqueous solution comprises subjecting said aqueous solution to gel filtration with a gel filtrating agent.

6. The process of claim 5, wherein the gel filtrating agent is selected from the group consisting of dextran gel, polyacrylamide gel, hydrophilic polyvinyl gel and porous glass beads.

7. Polysaccharide N9GIa obtained from the bark of *Melia azadirachta L.* which has the following characteristics:

the freeze dried product of said polysaccharide N9GIa is a white powder;
said polysaccharide N9GIa;
is a neutral polysaccharide which contains as the main chain thereof an $\alpha$-(1→4)-glucan connected to arabinose by an $\alpha$-(1→6) bond and is composed of glucose and arabinose at a ratio of about 5:1;
is soluble in water and insoluble in organic solvents selected from methanol, ethanol, acetone, ether, chloroform, ethyl acetate, benzene and hexane;
reacts with phenol sulfate and anthrone sulfate;
turns to greenish blue by reaction with iodine;
when analyzed by column gel chromatography using dextran gel with a fractionation range molecular weight of $1 \times 10^3 - 2 \times 10^5$ gives a single peak with a molecular weight of about 94,000;
has a specific rotation of $[\alpha]_D^{22}$: $-35°$ (c=0.4, H$_2$O);
has an infrared absorption spectrum as shown in FIG. 2, wherein $IR\nu_{max}.^{KBr}cm.^{-1}$: 3400, 2930, 1620;
has an ultraviolet absorption spectrum which shows no absorption maximum with end absorption only when measured in an aqueous solution; and
has a 100 MHz $^{13}$C nuclear magnetic resonance spectrum measured in deuterium oxide using TMS (tetramethylsilane) as the external standard as shown in FIG. 4.

8. A therapeutic composition characterized by inhibiting the growth of Sarcoma 180 transplanted tumor tissue in mice comprising an effective amount of the polysaccharide of claim 7 and a pharmaceutical diluent.

9. The therapeutic composition of claim 8 in unit dosage form wherein the effective amount per unit dosage is 10 to 500 mg.

10. A process for preparing polysaccharide N9GIa which comprises extracting the bark of *Melia azadirachta L.* with hot water and treating the hot water extract with a molecular sieve to thereby isolate said polysaccharide N9GIa having a molecular weight of about 94,000; said polysaccharide N9GIa having the following characteristics:

the freeze dried product of said polysaccharide N9GI is a white powder;
said polysaccharide N9GIa;
is a neutral polysaccharide which contains as the main chain thereof an $\alpha$-(1→4)-glucan connected to arabinose by an $\alpha$-(1→6) bond and is composed of glucose and arabinose at a ratio of about 5:1;
is soluble in water and insoluble in organic solvents selected from methanol, ethanol, acetone, ehter, chloroform, ethyl acetate, benzene and hexane;
reacts with phenol sulfate and anthrone sulfate;
turns to greenish blue by reaction with iodine;
when analyzed by column gel chromatography using dextran gel with a fractionation range molecular weight of $1 \times 10^3 - 2 \times 10^5$ gives a single peak with a molecular weight of about 94,000;
has a specific rotation of $[\alpha]_D^{22}$: $-35°$ (c=0.4, H$_2$O);
has an infrared absorption spectrum as shown in FIG. 2, wherein $IR\nu_{max}.^{KBr}cm.^{-1}$: 3400, 2930, 1620;
has an ultraviolet absorption spectrum which shows no absorption maximum with end absorption only when measured in an aqueous solution; and
has a 100 MHz $^{13}$C nuclear magnetic resonance spectrum measured in deuterium oxide using TMS (tetramethylsilane) as the external standard as shown in FIG. 4.

11. The process of claim 10, wherein the step of treating the hot water extract with a molecular sieve comprises treating the hot water extract with a molecular sieving agent having a fractionation range molecular weight from about $1 \times 10^3 - 1 \times 10^5$ to about $1 \times 10^3 - 1.5 \times 10^5$ to separate said hot water extract into three divided polysaccharide fractions, isolating and removing the first divided fraction and then treating said second and third divided fractions with a molecular sieving agent having a fractionation range molecular agent from about $1 \times 10^3 - 2 \times 10^5$ to about $1 \times 10^3 - 8 \times 10^5$ to thereby isolate said polysaccharide N9GIa.

12. The process of claim 11, wherein the step of treating said hot water extract comprises subjecting said hot water extract to filtration with a gel filtrating agent.

13. The process of claim 12, wherein the gel filtrating agent is selected from the group consisting of dextran gel, polyacrylamide gel, hydrophilic polyvinyl gel and porous glass beads.

14. Polysaccharide N9GIb obtained from the bark of *Melia azadirachta L.* which has the following characteristics:

the freeze dried product of said polysaccharide N9GIb is a white powder;
said polysaccharide N9GIb;

is a neutral polysaccharide which contains as the main chain thereof an $\alpha$-(1→4)-glucan interspersed with $\beta$-(1→3)-fucose and branched with $\alpha$-(1→6)-arabinose and is composed of glucose, arabinose and fucose at a ratio of about 5:2:1;

is soluble in water and insoluble in organic solvents selected from methanol, ethanol, acetone, ether, chloroform, ethyl acetate, benzene, and hexane;

reacts with phenol sulfate and anthrone sulfate;

turns greenish blue by reaction with iodine;

when analyzed by column gel chromatography using dextran gel with a fractionation range molecular weight of $1 \times 10^3 - 2 \times 10^5$ gives a single peak with a molecular weight of about 21,000;

has a specific rotation of $[\alpha]_D^{22}$: $-46°$ C. (c=0.28, $H_2O$);

has an infrared absorption spectrum as shown in FIG. 4, wherein $IR\nu_{max}.^{KBr}cm.^{-1}$: 3400, 2930, 1630;

has an ultraviolet absorption spectrum which shows no absorption maximum with end absorption only when measured in an aqueous solution;

has a 100 MHz $^{13}C$ nuclear magnetic resonance spectrum measured in deuterium oxide using TMS (tetramethylsilane) as the external standard as shown in FIG. 5.

15. A therapeutic composition characterized by inhibiting growth of Sarcoma 180 transplanted tumor tissue in mice comprising an effective amount of the polysaccharide of claim 14 and a pharmaceutical diluent.

16. The therapeutic composition of claim 15 in unit dosage form wherein the effective amount per unit dosage is 10 to 500 mg.

17. A process for preparing polysaccharide N9GIb which comprises extracting the bark of *Melia azadirachta L.* with hot water and treating the hot water extract with a molecular sieve to thereby isolate said polysaccharide N9GIb having a molecular weight of about 21,000; said polysaccharide N9GIb having the following characteristics:

the freeze dried product of said polysaccharide N9GIb is a white powder;

said polysaccharide N9GIb;

is a neutral polysaccharide which contains as the main chain thereof an $\alpha$-(1→4)-glucan interspersed with $\beta$-(1→3)-fucose and branched with $\alpha$-(1→6)-arabinose and is composed of glucose, arabinose and fucose at a ratio of about 5:2:1;

is soluble in water and insoluble in organic solvents selected from methanol, ethanol, acetone, ether, chloroform, ethyl acetate, benzene, and hexane;

reacts with phenol sulfate and anthrone sulfate;

turns greenish blue by reaction with iodine;

when analyzed by column gel chromatography using dextran gel with a fractionation range molecular weight of $1 \times 10^3 - 2 \times 10^5$ gives a single peak with a molecular weight of about 21,000;

has a specific rotation of $[\alpha]_D^{22}$: $-46°$ C. (c=0.28, $H_2O$);

has an infrared absorption spectrum as shown in FIG. 4, wherein $IR\nu_{max}.^{KBr}cm.^{-1}$: 3400, 2930, 1630;

has an ultraviolet absorption spectrum which shows no absorption maximum with end absorption only when measured in an aqueous solution;

has a 100 MHz $^{13}C$ nuclear magnetic resonance spectrum measured in deuterium oxide using TMS (tetramethylsilane) as the external standard as shown in FIG. 5.

18. The process of preparing the polysaccharide N9GIb of claim 17, wherein the step of treating the hot water extract with a molecular sieve comprises treating the hot water extract with a molecular sieving agent having a fractionation range molecular weight from about $1 \times 10^3 - 1 \times 10^5$ to about $1 \times 10^3 - 1.5 \times 10^5$ to separate said hot water extract into three divided polysaccharide fractions, isolating and removing the first divided fraction and the treating said second and third divided fractions with a molecular sieving agent having a fractionation range molecular agent from about $1 \times 10^3 - 2 \times 10^5$ to about $1 \times 10^3 - 8 \times 10^5$ to thereby isolate said polysaccharide N9GIb.

19. The process of claim 18, wherein the step of treating the hot water extract comprises subjecting said hot water extract to gel filtration with a gel filtrating agent.

20. The process of claim 19, wherein the gel filtrating agent is selected from the group consisting of dextran gel, polyacrylamide gel, hydrophilic polyvinyl gel and porous glass beads.

* * * * *